United States Patent [19]

Wade et al.

[11] 4,007,191

[45] Feb. 8, 1977

[54] 2-PIPERIDINYL OR TETRAHYDROPYRIDINYL)-ALKYL)-2,3-DIHYDRO-3-HYDROXY-1H-BENZ-(DE)ISOQUINOLIN-1-ONES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Oct. 14, 1975

[21] Appl. No.: 621,939

[52] U.S. Cl. .................. 260/288 CF; 260/256.4 R; 260/250 AH; 260/250 BN; 260/268 TR; 260/281 GN; 424/258

[51] Int. Cl.² ........................................ C07D 401/06

[58] Field of Search ............. 424/250; 260/268 TR, 260/249.5, 293.62, 295 J, 256.4 R, 256.4 C, 293.59, 288 CF

[56] References Cited

UNITED STATES PATENTS

| | | | |
|---|---|---|---|
| 3,935,227 | 1/1976 | Wade et al. | 260/281 S |
| 3,940,397 | 2/1976 | Wade et al. | 260/268 TR |
| 3,940,398 | 2/1976 | Wade et al. | 260/268 TR |

*Primary Examiner*—Donald G. Daus
*Assistant Examiner*—Jose Tovar
*Attorney, Agent, or Firm*—Lawrence S. Levinson; Merle J. Smith; Stephen B. Davis

[57] ABSTRACT

Compounds of the following formula

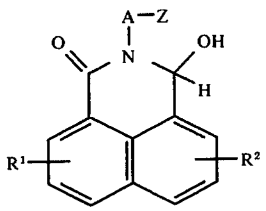

wherein $R^1$ and $R^2$ are selected from hydrogen, lower alkyl, lower alkoxy, lower alkylthio, halogen, trifluoromethyl, nitro,amino and cyano; Z is selected from

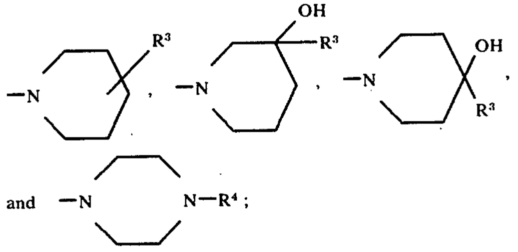

$R^3$ is selected from phenyl, phenyl-lower alkyl, substituted phenyl, and substituted phenyl-lower alkyl; $R^4$ is selected from $R^3$ and a 6-membered unsaturated substituted or unsubstituted heterocyclic ring selected from pyridine, diazine and triazine; and A is a straight or branched chainalkylene of 2 to 8 carbons are disclosed. These comounds exhibit antidepressant activity.

15 Claims, No Drawings

2-(PIPERIDINYL OR TETRAHYDROPYRIDINYL)-ALKYL)-2,3-DIHYDRO-3-HYDROXY-1H-BENZ(DE)ISOQUINOLIN-1-ONES

SUMMARY OF THE INVENTION

This invention relates to new 2-[(substituted piperazinyl, piperidinyl, or tetrahydropyridinyl)alkyl]-2,3-dihydro-3-hydroxy-1H-benz[de]isoquinolin-1-ones of the formula (I)

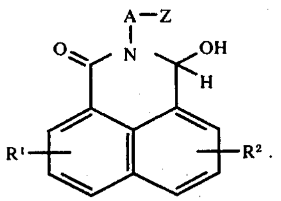

$R^1$ and $R^2$ are each independently selected from hydrogen, halogen, trifluoromethyl, lower alkyl, lower alkoxy, lower alkylthio, amino, nitro and cyano.

A is straight or branched chain alkylene of 2 to 8 carbons.

Z is selected from

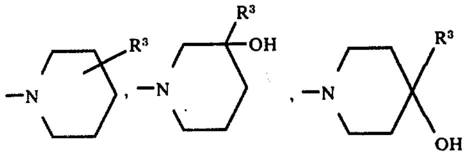

, and

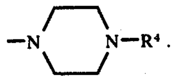

$R^3$ is phenyl, phenyl-lower alkyl, substituted phenyl or substituted phenyl-lower alkyl.

$R^4$ is $R^3$ or a 6-membered substituted or unsubstituted unsaturated heterocyclic ring selected from pyridine, diazine, and triazine attached to the 4-position of the piperazinyl by way of a carbon atom.

In the definition of Z the dashed line indicates the optional presence of a double bond.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The phenyl-lower alkyl groups include such lower alkyl groups attached to a phenyl, e.g., benzyl, phenethyl, etc. The lower alkylthio group include such lower alkyl groups attached to a sulfur, e.g., methylthio, ethylthio, etc.

Straight or branched chain alkylene of 2 to 8 carbons is intended to include groups such as $-(CH_2)_n-$ wherein $n$ is 2 to 8,

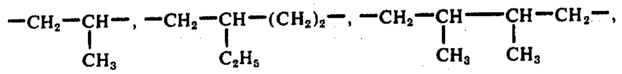

etc.

The substituted phenyl and phenyl-lower alkyl groups include one or two substituents selected from lower alkyl, lower alkoxy, lower alkylthio, halogen, $CF_3$, nitro, and amino provided that only one phenyl substituent is $CF_3$, nitro, amino or lower alkylthio. Examples of the type of groups contemplated are o-, m- or p-chlorophenyl, o-, m-, or p-tolyl, 2,5-dibromophenyl, 3,5-dimethylphenyl, o-, m-, or p-methoxybenzyl, o-, m-, or p-chlorobenzyl, o-, m-, or p-methoxybenzyl, o-, m-, or p-bromophenethyl, etc.

The term "halogen" as used throughout this specification refers to fluorine, bromine, chlorine, and iodine, with fluorine, bromine and chlorine being preferred and chlorine being most preferred.

The terms "diazine" and "triazine" are meant to include the various isomeric forms, i.e. pyrimidine, pyridazine, pyrazine, s-triazine, a-triazine, and v-triazine. The pyridine, diazine or triazine can be substituted at one or two available carbon atoms by a lower alkyl, lower alkoxy or halogen group.

Preferred compounds of this invention are those having the formula (Ia)

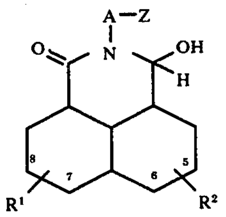

$R^1$ and $R^2$ are the same and are selected from hydrogen, Cl, Br, F, methyl, and methoxy and are located at the 7- and 6-positions or the 8- and 5-positions respectively.

Z is selected from

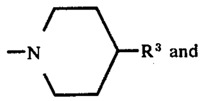

and

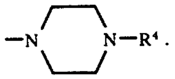

$R^3$ is selected from phenyl, benzyl, phenethyl, monosubstituted phenyl, monosubstituted benzyl, and monosubstituted phenethyl wherein said substituent is Cl, Br, F, methyl or methoxy.

$R^4$ is selected from $R^3$, 2-pyridinyl, 2-pyrimidinyl, 2,4,6-triazinyl, substituted 2-pyridinyl, substituted 2-pyrimidinyl, and substituted 2,4,6-triazinyl wherein said substituent is a methyl, methoxy, or Cl group attached to one or two available carbon atoms.

A is straight or branched chain alkylene of 2 to 6 carbons.

The most preferred compounds are of those of formula Ia wherein $R^1$ and $R^2$ are both hydrogen; A is straight chain alkylene of 2 to 6 carbons, especially $-(CH_2)_2-$.

The new compounds of this invention are prepared by reducing a compound of the formula

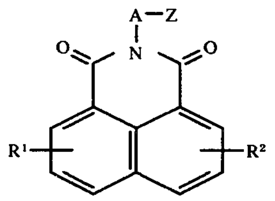

(II)

with a borohydride such as sodium borohydride. This reduction reaction is performed in presence of an organic solvent, preferably a mixture of dioxane and ethanol, at room temperature for several days.

The compounds of formula II wherein Z is substituted piperidinyl or tetrahydropyridinyl are disclosed in U.S. Ser. No. 501,411 filed Aug. 28, 1974, now U.S. Pat. 3,935,227. The compounds of formula II wherein Z is phenyl or phenyl-lower alkyl substituted piperazinyl are disclosed in U.S. Ser. No. 523,293 filed Nov. 13, 1974, now U.S. Pat. 3,940,397. The compounds of formula II wherein Z is hetero substituted piperazinyl are disclosed in U.S. Ser. No. 543,558 filed Jan. 23, 1975, now U.S. Pat. 3,940,398.

As disclosed in these applications, the compounds of formula II wherein A is straight or branched chain alkylene of 2 to 8 carbons are prepared by reacting a substituted naphthalic anhydride of the formula

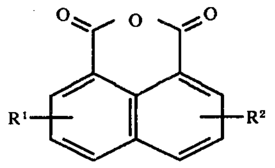

(III)

with an alkanolamine of the formula (IV) $H_2N-A-OH$ to yield the alcohol of the formula

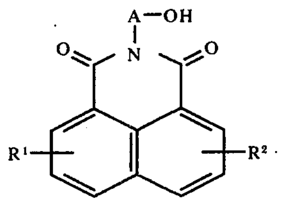

(V)

The alcohol of formula V is converted to the intermediate of formula

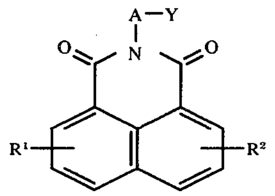

(VI)

where Y is a leaving group such as tosylate, methanesulfonate or halogen by treating the alcohol with reagents such as p-toluenesulfonyl chloride, methanesulfonyl chloride, thionyl chloride, thionyl bromide or hydrogen iodide.

The intermediate of formula VI is then converted to the starting materials of formula II by reactions with compounds of the formula HZ.

The substituted naphthalic anhydride of formula III can be converted directly to the starting materials of formula II by reacting the anhydride with compounds of the formula (VII) $H_2N-A-Z$.

Also, the intermediate of formula VI can be prepared by combining a substituted naphthalimide of the formula

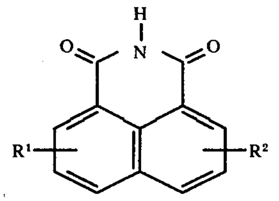

(VIII)

in an organic solvent such as dimethylformamide (DMF) with a polar organic solvent solution of a base, as for example an alcohol solution of potassium hydroxide, followed by the addition of a solution of the compound of the formula (IX) $Y'-A-Y$ wherein Y' and Y are the same or different and are leaving groups selected from tosylate, methanesulfonate, or halogen and A is a straight or branched chain alkylene of 2 to 8 carbons.

Alternatively, the compounds of formula II wherein A is straight or branched alkylene of 2 to 8 carbons can be prepared by combining the anion of the substituted naphthalimide of formula VIII, described above, with a solution of the compound of the formula (X) $Y-A-Z$ wherein Y is a leaving group as previously defined.

The various starting materials such as the substituted anhydrides of formula III and the alcohols of formula V and the substituted naphthalimides of formula VIII are known in the art or are readily obtainable by known procedures. Further process details are also provided in the illustrative examples.

The compounds of formula II wherein either or both $R^1$ and $R^2$ are amine or $R^3$ is an amino substituted phenyl or phenyl-lower alkyl are prepared by reducing the corresponding nitro substituted compound with a reducing agent such as hydrogen over a palladium catalyst or a suitable chemical reducing agent. This is preferably done as the last step in the reaction sequence for preparing the intermediate of formula II.

The new compounds of the present invention are capable of modifying the central nervous system. When administered to mice, cats, rats, dogs, and other mammalian species in amounts ranging from about 0.5 mg. to about 400 mg. per kg. of body weight per day, these compounds in particular exhibit antidepressant activity. A preferred dosage regimen for optimum results would be from about 35 mg. to about 3 g. of active ingredient in single or divided doses administered in a 24 hour period.

The antidepressant activity of the compounds of formula I is demonstrated by their ability to block the reuptake of monoamines in vitro according to the procedure of Horn et al. (*Molecular Pharmacology*, 7th Ed., ( 1971), page (66).

For this pharmaceutical purpose a compound or mixture of compounds of formula I may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

2-[2-(3,6-Dihydro-4-phenyl-1(2H)-pyridinyl)ethyl[-2,3-dihydro-3-hydroxy-1H-benz[de]isoquinolin-1-one a. 2-[4-(3,6-Dihydro-4-phenyl)-1-(2H)-pyridinyl)-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b. 2-(2-Hydroxyethyl)-1H-benz[de]isoquinoline-1,3(2H)-dione, 4-methylbenzenesulfonate ester 52 g. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c. 2-[2-(3,6-Dihydro-4-phenyl-1-(2H)-pyridinyl)ethyl]-1H-benz[de]isoquinoline-1,3(2H)-dione, hydrochloride (1:1)

10 g. (0.025 mole) of the ester from part (b) and 8.1 g. (0.051 mole) of 4-phenyl-1,2,3,6-tetrahydropyridine (freed from the hydrochloride salt with aqueous NaOH, extracted into toluene and dried over 4A molecular sieves) are refluxed in 300 ml. of toluene for one hour. The mixture is then cooled to 25° for three hours and the resulting precipitate filtered off. The filtrate is shaken with excess 10% HC1 (aqueous) producing a gum that is insoluble in both layers. After several minutes the gum crystallizes and is filtered from the two liquid phases. Recrystallization of the filter cake from 600 ml. of 95% ethanol and drying at 80° (0.1 mm.) for two hours produces 3.5 g. of 2-[2-(3,6-dihydro-4-phenyl-1(2H)-pyridinyl)ethyl]-1H-benz[de]isoquinoline-1,3(2H)-dione, hydrochloride (1:1); preliminary melting at 279° and final melting with decomposition at 283°–285°.

d. 2-[2-(3,6-Dihydro-4-phenyl-1(2H)-pyridinyl)ethyl]-2,3-dihydro-3-hydroxy-1H-benz[de]isoquinolin-1-one 10 g. (0.0238 moles) of the hydrochloride salt product from part (c) is dissolved in $CHCl_3$ and washed with 5% KOH, twice with water, and dried ($Na_2SO_4$). The chloroform is evaporated and the residue is dissolved in 400 ml. of dioxane/ethanol (1:1). Sodium borohydride is added to the solution (5.0 g. on the first day and 7.0 g. on the second day) and the mixture is stirred at room temperature for three days. The solution is evaporated to dryness and the residue is taken up in chloroform and washed with saturated $NaHCO_3$, twice with water, and dried ($Na_2SO_4$). The chloroform is evaporated and the residue is recrystallized from chloroform/ethanol to yield 4.75 g. of 2-[2-(3,6-dihydro-4-phenyl-1(2H)-pyridinyl)ethyl]-2,3-dihydro-3-hydroxy-1H-benz[de]isoquinolin-1-one; m.p. 182°–183° (dec.).

EXAMPLE 2

2-[3-(3,6-Dihydro-4-phenyl)-1(2H)-pyridinyl)propyl]-2,3-dihydro-3-hydroxy-1H-benz[de]isoquinoline-1-one a. 2-(3-Hydroxypropyl)-1H-benz[de]isoquinoline-1,3(2H)-dione, 4-methylbenzenesulfonate ester Following the procedure of example 1(a) and (b) but substituting 3-aminopropanol for the ethanolamine in part (a) one obtains 2-(3-hydroxypropyl)-1H-benz[de]isoquinoline-1,3(2H)-dione, 4-methylbenzenesulfonate ester.

b. 2-[3-(3,6-Dihydro-4-phenyl-1(2H)-pyridinyl)-propyl]-1H-benz[de]isoquinoline-1,3(2H)-dione, hydrochloride (1:1)

10.3 g. (0.025 mole) of the ester from part (a) and 8.1 g. (0.051 mole) of 4-phenyl-1,2,3,6-tetrahydropyridine (freed from the hydrochloride salt with aqueous NaOH, extracted into toluene and dried over 4A molecular sieves) are refluxed in 300 ml. of toluene for one hour. The mixture is then cooled to 25° for three hours and the resulting precipitate filtered off. The filtrate is shaken with excess 10% HCl (aqueous) producing a gum that is insoluble in both layers. After several minutes the gum crystallizes and is filtered from the two liquid phases. Recrystallizations of the filter cake from 95% ethanol and drying at 80° (0.1mm.) for two hours produces 3.5 g. of 2-[3-(3,6-dihydro-4-phenyl-1-(2H)-pyridinyl)propyl]-1H-benz[de]isoquino-line-1,3(2H)-dione, hydrochloride (1:1); which darkens at 242° and melts at 244°–245.5°.

c. 2-[3-(3,6-Dihydro-4-phenyl)-1(2H)-pyridinyl)-propyl]-2,3-dihydro-3-hydroxy-1H-benz-[de]isoquinolin-1-one The hydrochloride salt product from part (b) is treated according to the procedure of example 1(d) to yield the titled compound.

EXAMPLE 3

2-[4-(3,6-Dihydro-4-phenyl)-1(2H)-pyridinyl)butyl]-2,3-dihydro-3-hydroxy-1H-benz[de]isoquinolin-1-one a. 2-(4-Hydroxybutyl)-1H-benz[de]isoquinoline-1,3(2H)-dione, 4-methylbenzenesulfonate ester Following the procedure of example 1(a) and (b) but substituting 4-aminobutanol for the ethanolamine in part (a) one obtains 2-(4-hydroxybutyl)-1H-benz-[de]isoquinoline-1,3(2H)-dione, 4-methylbenzenesulfonate ester.

b. 2-[4-(3,6-Dihydro-4-phenyl-1(2H)-pyridinyl)butyl]-1H-benz[de]isoquinoline-1,3(2H)-dione, hydrochloride (1:1)

10.6 g. (0.025 mole) of the ester from part (a) and 8.1 g. (0.051 mole) of 4-phenyl-1,2,3,6-tetrahydropyridine (freed from the hydrochloride salt with aqueous NaOH, extracted into chloroform and stripped of solvent) are refluxed in 300 ml. of toluene for one hour. The mixture is then cooled to 25° for three hours and the resulting precipitate filtered off. The filtrate is shaken with excess 10% HCl (aqueous), producing a gum that is insoluble in both layers. After several minutes, the gum crystallizes and is filtered from the two liquid phases. Recrystallization of the filter cake from ethanol-chloroform (2:1) and drying at 80° (0.1 mm.) for ten hours produces 9.8 g. of 2-[4-(3,6-dihydro-4-phenyl-1(2H)-pyridinyl)butyl]-1H-benz[de]isoquinoline-1,3(2H)-dione, hydrochloride (1:1); m.p. 250°–252°.

c. 2-[4-(3,6-Dihydro-4-phenyl)-1-(2H)-pyridinyl)-butyl]-2,3-dihydro-3-hydroxy-1H-benz[de]isoquinolin-1-one The hydrochloride salt product from part (b) is treated according to the procedure of example 1(d) to yield the titled compound.

EXAMPLE 4

2-[6-(3,6-Dihydro-4-phenyl-1(2H)-pyridinyl)hexyl]-2,3-dihydro-3-hydroxy-1H-benz[de]isoquinolin-1-one a. 2-(6-Bromohexyl)-1H-benz[de]-isoquinoline-1,3(2H)-dione 100 g. (0.5 mole) of 1,8-naphthalimide are suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g. (1.0 mole) of 1,6-dibromohexane are added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(6-bromohexyl)-1H-benz-[de]isoquinoline-1,3(2H)-dione. The precipitate is filtered off, washed with fresh hexane and dried for 2 hours at 50° (0.1 mm.) to yield 148 g. of 2-(6-bromohexyl)-1H-benz[de]isoquinoline-1,3(2H)-dione. An analytically pure sample is prepared by dissolving the above product in hot 95% ethanol and recrystallizing by allowing the solution to cool to 25°. The resulting precipitate is dried for two hours at 50° (0.1 mm.) to yield pure 2-(6-bromohexyl)-1H-benz[de]isoquinoline-1,3(2H)-dione, m.p. 95°–96°.

b. 2-[6-(3,6-Dihydro-4-phenyl-1(2H)-pyridinyl)hexyl]-1H-benz[de]isoquinoline-1,3(2H)-dione, hydrochloride (1:1)

18 g. (0.05 mole) of 2-(6-bromohexyl)-1H-benz-[de]isoquinoline-1,3(2H)-dione, from part (a), 8.8 g. (0.055 mole) of 4-phenyl-1,2,3,6-tetrahydropyridine (obtained from hydrochloride salt), and 6.5 g. (0.05 mole) of diisopropylethylamine are refluxed in 500 ml. of toluene for 4 hours. The reaction mixture is washed with 10% potassium hydroxide and the toluene solution is then filtered. The filtrate is shaken with excess 10% HCl forming slowly crystallizing oil. The precipitate is filtered from the two liquid phases and recrystallized from hot 95% ethanol which contains sufficient $CHCl_3$to get all of the material into the hot solution. The resulting material is dried for 2 hours at 50° (0.1 mm.) to yield 9.0 g. of 2-[6(3,6-dihydro-4-phenyl-1(2H)-pyridinyl)hexyl]-1H-benz[de]isoquinoline-1,3(2H)-dione, hydrochloride (1:1); m.p. 259°–261°.

c. 2-[6-(3,6-Dihydro-4-phenyl-1(2H)-pyridinyl)hexyl]-2,3-dihydro-3-hydroxy-1H-benz[de]isoquinolin-1-one The hydrochloride salt product from part (b) is treated according to the procedure of example 1(d) to yield the titled compound.

EXAMPLE 5

2-[5-(3,6-Dihydro-4-phenyl-1-(2H)-pyridinyl)pentyl]-2,3-dihydro-3-hydroxy-1H-benz[de]isoquinolin-1-one a. 2-(5-Bromopentyl)-1H-benz[de]isoquinoline-1,3(2H)-dione Following the procedure of part (a) of example 4 but substituting 1,5-dibromopentane for the 1,6-dibromohexane, one obtains 2-(5-bromopentyl)-1H-benz[de]isoquinoline-1,3(2H)-dione; m.p. 113°–115°.

b. 2-[5-(3,6-Dihydro-4-phenyl-1(2H)-pyridinyl)pentyl]-1H-benz[de]isoquinoline-1,3(2H)-dione, hydrochloride (1:1)

Following the procedure of part (b) of example 4 but substituting 2-(5-bromopentyl)-1H-benz[de]isoquinoline-1,3(2H)-dione for the 2-(6-bromohexyl)-1H-benz-[de]isoquinoline-1,3(2H)-dione, one obtains 2-[5-(3,6-dihydro-4-phenyl-1(2H)-pyridinyl)pentyl]-1H-benz[de]isoquinoline-1,3(2H)-dione, hydrochloride (1:1). The product is purified by recrystallization from n-butanol; m.p. 207°–210°.

c. 2-[5-(3,6-Dihydro-4-phenyl-1(2H)-pyridinyl)pentyl]-2,3-dihydro-3-hydroxy-1H-benz[de]isoquinolin-1-one The hydrochloride salt product from part (b) is treated according to the procedure of example 1(d) to yield the titled compound.

EXAMPLE 6

2-[2-(3,6-Dihydro-4-(chlorophenyl)-1(2H)-pyridinyl-)ethyl]-2,3-dihydro-3-hydroxy-1H-benz[de]isoquinolin-1-one a. 2-[2-[(4-Chlorophenyl)-3,6-dihydro-1(2H)-pyridinyl]ethyl]-1H-benz[de]isoquinoline-1,3(2H)-dione, hydrochloride (1:1)

8.7 g. (0.022 mole) of the ester from Example 1(b) and 7.8 g. (0.040 mole) of 4-(p-chlorophenyl)-1,2,3,6-tetrahydropyridine freed from the hydrochloride salt with aqueous NaOH and extracted into toluene) are refluxed in 250 ml. of toluene for one hour. The mixture is then cooled to 25° for three hours and the resulting precipitate filtered off. The filtrate is shaken with excess 10% HCl (aqueous) producing a precipitate that is insoluble in both layers. After several minutes the precipitate is filtered from the two liquid phases. Recrystallization of the filter cake (by dissolving in 1 liter of hot 8:2 $CHCl_3$:EtOH, concentrating to 300 ml. and cooling), followed by drying at 80° (0.1 mm.) for two hours produces 5.6 g. of 2-[2-[(4-chlorophenyl)-3,6dihydro-1(2H)-pyridinyl]ethyl]-1H-benz[de]isoquinoline-1,3(2H)-dione, hydrochloride (1:1); m.p. 287°–288° (dec.).

b. 2-[2-(3,6-Dihydro-4-(chlorophenyl)-1(2H)-pyridinyl)ethyl]-2,3-dihydro-3-hydroxy-1H-benz[de]isoquinolin-1-one The hydrochloride salt product from part (a) is treated according to the procedure of example 1(d) to yield the titled compound.

EXAMPLES 7–28

Following the procedure of example 1 but substituting for the 4-phenyl-1,2,3,6-tetrahydropyridine an equivalent amount of one of the following:

- 2-phenyl-1,2,3,6-tetrahydropyridine
- 3-phenyl-1,2,3,6-tetrahydropyridine
- 5-phenyl-1,2,3,6-tetrahydropyridine
- 6-phenyl-1,2,3,6-tetrahydropyridine
- 4-(phenylmethyl)-1,2,3,6-tetrahydropyridine
- 4-(2-phenylethyl)-1,2,3,6-tetrahydropyridine
- 4-(3-phenylpropyl)-1,2,3,6-tetrahydropyridine
- 4-(4-phenylbutyl)-1,2,3,6-tetrahydropyridine
- 3-(phenylmethyl)-1,2,3,6-tetrahydropyridine
- 4-(4-fluorophenyl)-1,2,3,6-tetrahydropyridine
- 4-(3-trifluoromethylphenyl)-1,2,3,6-tetrahydropyridine
- 4-(3,4-dichlorophenyl)-1,2,3,6-tetrahydropyridine
- 4-(2-bromophenyl)-1,2,3,6-tetrahydropyridine
- 4-(3-methylphenyl)-1,2,3,6-tetrahydropyridine
- 4-(2-ethoxyphenyl)-1,2,3,6-tetrahydropyridine
- 4-(4-nitrophenyl)-1,2,3,6-tetrahydropyridine
- 3-(4-chlorophenyl)-1,2,3,6-tetrahydropyridine
- 2-(4-nitrophenyl)-1,2,3,6-tetrahydropvridine
- 4-[(4-chlorophenyl)methyl]-1,2,3,6-tetrahydropyridine
- 4-[2-(4-fluorophenyl)ethyl]-1,2,3,6-tetrahydropyridine
- 4-[3-(3-ethylphenyl)propyl]-1,2,3,6-tetrahydropyridine
- 3-(2-bromophenyl)methyl-1,2,3,6-tetrahydropyridine one obtains

- 2-[2-(3,6-dihydro-2-phenyl-1(2H)-pyridinyl)ethvl]-2,3-dihydro-3-hydroxy-1H-benz[de]isoquinolin-1-one;
- 2-[2-(3,6-dihydro-3-phenyl-1(2H)-pyridinyl)ethyl]-2,3-dihydro-3-hydroxy-1H-benz[de]isoquinolin-1-one;
- 2-[2-(3,6-dihydro-5-phenyl-1(2H)-pyridinyl)ethyl]-2,3-dihydro-3-hydroxy-1H-benz[de]isoquinolin-1-one;
- 2-[2-(3,6-dihydro-6-phenyl-1(2H)-pyridinyl)ethyl]-2,3-dihydro-3-hydroxy-1H-benz[de]isoquinolin-1-one;
- 2-[2-(3,6-dihydro-4-(phenylmethyl)-1(2H)-pyridinyl)ethyl]-2,3-dihydro-3-hydroxy-1H-benz[de]isoquinolin-1-one;
- 2-[2-(3,6-dihydro-4-(2-phenylethyl)-1(2H)-pyridinyl)ethyl]-2,3-dihydro-3-hydroxy-1H-benz[de]isoquinolin-1-one;
- 2-[2(3,6-dihydro-4-(3-phenylpropyl)-1(2H)-pyridinyl)ethyl]-2,3-dihydro-3-hydroxy-1H-benz[de]isoquinolin-1-one;
- 2-[2-(3,6-dihydro-4-(4-phenylbutyl)-1(2H)-pyridinyl)ethyl]-2,3-dihydro-3-hydroxy-1H-benz[de]isoquinolin-1-one;
- 2-[2-(3,6-dihydro-3-(phenylmethyl)-1(2H)-pyridinyl)ethyl]-2,3-dihydro-3-hydroxy-1H-benz[de]isoquinolin-1-one;
- 2-[2-(3,6-dihydro-4-(4-fluorophenyl)-1(2H)-pyridinyl)ethyl]-2,3-dihydro-3-hydroxy-1H-benz[de]isoquinolin-1one;
- 2-[2-(3,6-dihydro-4-(3-trifluoromethylphenyl)-1(2H)-pyridinyl)-ethyl]-2,3-dihydro-3-hydroxy-1H-benz[de]isoquinolin-1-one;
- 2-[2-(3,6-dihydro-4-(3,4-dichlorophenyl)-1(2H)-pyridinyl)ethyl]-2,3-dihydro-3-hydroxy-1H-benz[de]isoquinolin-1-one;
- 2-[2-(3,6-dihydro-4-(2-bromophenyl)-1(2H)-pyridinyl)-ethyl]-2,3-dihydro-3-hydroxy-1H-benz[de]isoquinolin-1-one;
- 2-[2-(3,6-dihydro-4-(3-methylphenyl)-1(2H)-pyridinyl)-ethyl]-2,3-dihydro-3-hydroxy-1H-benz[de]isoquinolin-1one;
- 2-[2-(3,6-dihydro-4-(2-ethoxyphenyl)-1(2H)-pyridinyl)ethyl]-2,3-dihydro-3-hydroxy-1H-benz[de]isoquinolin-1-one;
- 2-[2-(3,6-dihydro-4-(4-nitrophenyl)-1(2H)-pyridinyl)ethyl]-2,3-dihydro-3-hydroxy-1H-benz[de]isoquinolin-1-one;
- 2-[2-(3,6-dihydro-3-(4-chlorophenyl)-1(2H)-pyridinyl)ethyl]-2,3-dihydro-3-hydroxy-1H-benz[de]isoquinolin-1-one;
- 2-[2-(3,6-dihydro-2-(4-nitrophenyl)-1(2H)-pyridinyl)ethyl]-2,3-dihydro-3-hydroxy-1H-benz[de]isoquinolin-1-one;
- 2-[2-(3,6-dihydro-4-[(4-chlorophenyl)methyl]-1(2H)-pyridinyl)-ethyl]-2,3-dihydro-3-hydroxy-1H-benz[de]isoquinolin-1-one;
- 2-[2-(3,6-dihydro-4-[2-(4-fluorophenyl)ethyl]-1(2H)-pyridinyl)ethyl]-2,3-dihydro-3-hydroxy-1H-benz[de]isoquinolin-1-one;
- 2-[2-(3,6-dihydro-4-[3-(3-ethylphenyl)propyl]-1(2H)-pyridinyl)ethyl]-2,3-dihydro-3-hydroxy-1H-benz[de]isoquinolin-1-one; and
- 2-[2-(3,6-dihydro-3-[(2-bromophenyl)methyl]-1(2H)-pyridinyl)-ethyl]-2,3-dihydro-3-hydroxy-1H-benz[de]isoquinolin-1-one; respectively.

Similarly, by employing the tetrahydropyridine reactants of examples 6 to 28 within the procedures of examples 2 to 5, other compounds within the scope of this invention are prepared.

EXAMPLES 29–37

Following the procedure of example 1 but substituting the alkanolamine shown in Col. I for the ethanolamine the following products are obtained wherein A is the radical shown in Col. II.

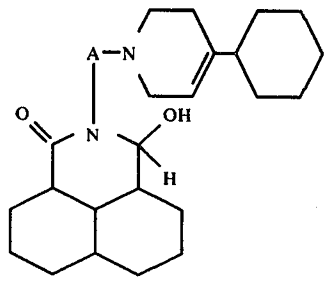

| Ex. | Col. I | Col. II |
|---|---|---|
| 29 | $H_2N-(CH_2)_5-OH$ | $-(CH_2)_5-$ |
| 30 | $H_2N-(CH_2)_6-OH$ | $-(CH_2)_6-$ |
| 31 | $H_2N-(CH_2)_7-OH$ | $-(CH_2)_7-$ |
| 32 | $H_2N-(CH_2)_8-OH$ | $-(CH_2)_8-$ |
| 33 | $H_2N-CH_2-CH(CH_3)-CH_2-OH$ | $-CH_2-CH(CH_3)-CH_2-$ |
| 34 | $H_2N-CH(CH_3)-(CH_2)_3-OH$ | $-CH(CH_3)-(CH_2)_3-$ |
| 35 | $H_2N-(CH_2)_3-CH(CH_3)-OH$ | $-(CH_2)_3-CH(CH_3)-$ |
| 36 | $H_2N-CH_2-CH(C_3H_7)-(CH_2)_2-OH$ | $-CH_2-CH(C_3H_7)-(CH_2)_2-$ |
| 37 | $H_2N-CH(CH_3)-CH_2-CH(CH_3)-OH$ | $-CH(CH_3)-CH_2-CH(CH_3)-$ |

Similarly, by employing the alkanolamines of examples 29 to 37 within the procedures of examples 6 to 28, other compounds within the scope of this invention are obtained.

EXAMPLE 38

2-[2-[4-(Phenylmethyl)-1-piperidinyl]-2,3-dihydro-3-hydroxy-1H-benz[de]isoquinolin-1-one a. 2-[2-[4-(Phenylmethyl)-1-piperidinyl]ethyl]-1H-benz[de]isoquinoline-1,3 (2H)-dione, hydrochloride (1:1)

10 g. (0.025 mole) of the ester from Example 1 (b) and 9 g. (0.051 mole) of (4-phenylmethyl)piperidine are refluxed in 300 ml. of toluene for one hour, the solution becoming homogeneous at the reflux temperature. The mixture is then cooled to 25° for three hours and the resulting precipitate filtered off. The filtrate is washed with 10% NaOH then shaken with excess 10% HCl (aqueous) to produce a gum that is insoluble in both layers. After several minutes the gum crystallizes and is filtered from the two liquid phases. Recrystallization of the filter cake from 50% aqueous ethanol and drying at 85° (0.1 mm.) for 2 hours produces 7.2 g. of 2-[2-[4-(phenylmethyl)-1-piperidinyl]ethyl]-1H-benz-[de]isoquinoline-1,3 (2H)-dione, hydrochloride (1:1); m.p. 242°–244°.

b. 2-[2-[4-(Phenylmethyl)-1-piperidinyl]ethyl]-2,3-dihydro-3-hydroxy-1H-benz[de]isoquinolin-1-one 10 g. (0.023 moles) of the hydrochloride salt product from part (a) are dissolved in chloroform and washed with 5% KOH and twice with water. The chloroform is evaporated and the residue is dissolved in 500 ml. of dioxane/ethanol (1:1). 5 g. of sodium borohydride are added and the mixture is stirred for two days at room temperature. The reaction mixture is then evaporated to dryness and the residue is taken up in chloroform. The chloroform solution is washed with 10% KOH, twice with water, dried ($Na_2SO_4$), and evaporated. The residue is recrystallized from chloroform/ethanol to yield 2.97 of 2-[2-[4-(phenylmethyl)-1-piperidinyl]ethyl]-2,3-dihydro-3-hydroxy-1H-benz[de]isoquinolin-1-one, m.p. 153°–155°.

EXAMPLE 39

2-[2-(4-Phenyl-1-piperidinyl)ethyl]-2,3-dihydro-3-hydroxy-1H-benz[de]isoquinolin-1-one a. 2-[2-(4-Phenyl-1-piperidinyl)ethyl]-1H-benz-[de]isoquinoline-1,3 (2H)-dione, hydrochloride (1:1)

10 g. (0.025 mole) of the ester from example 1 (b), and 8.2 g. (0.051 mole) of 4-phenylpiperidine are refluxed in 300 ml. of toluene for one hour. The mixture is then cooled to 25° for three hours and the resulting precipitate filtered off. The filtrate is shaken with excess 10% HCl (aqueous) producing a gum that is insoluble in both layers. After several minutes the gum crystallizes and is filtered from the two liquid phases. Recrystallization of the filter cake from 50% aq. ethanol and drying at 25° (200 mm.) for three days produces 8.8 g. of 2-[2-(4-phenyl-1-piperidinyl)ethyl]-1H-benz-[de]isoquinoline-1,3 (2H)-dione, hydrochloride (1:1); m.p. 272°–274°.

b. 2-[2-(4-Phenyl-1-piperidinyl)ethyl]-2,3-dihydro-3-hydroxy-1H-benz[de]isoquinolin-1-one The hydrochloride salt product from part (a) is treated according to the procedure of example 38 (b) to yield the titled compound.

EXAMPLE 40

2-[3-(4-Phenyl-1-piperidinyl)propyl]-2,3-dihydro-3-hydroxy-1H-benz[de]isoquinolin-1-one a. 2-[3-(4-Phenyl-1-piperidinyl)propyl]-1H-benz-[de]isoquinoline-1,3 (2H)-dione, hydrochloride (1:1)

Following the procedure of example 2 (a) but substituting an equivalent amount of 4-phenylpiperidine for the 4-phenyl-1,2,3,6-tetrahydropyridine, one obtains 2-[3-(4-phenyl-1-piperidinyl)propyl]-1H-benz-[de]isoquinoline-1,3 (2H)-dione, hydrochloride.

b. 2-[3-(4-Phenyl-1-piperidinyl)propyl]-2,3-dihydro-3-hydroxy-1H-benz[de]isoquinolin-1-one The hydrochloride salt product from part (a) is treated according to the procedure of example 38 (b) to yield the titled compound.

EXAMPLE 41

2-[4-(4-Phenyl-1-piperidinyl)butyl]-2,3-dihydro-3-hydroxy-1H-benz[de]isoquinolin-1-one a. 2-(4-Bromobutyl)-1H-benz[de] isoquinoline-1,3 (2H)-dione 100 g. (0.5 mole) of 1,8-naphthalimide is suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g.(1.0 mole) of 1,4-dibromobutane is added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(4-bromobutyl)-1H-benz[de] isoquinoline-1,3 (2H)-dione. The precipitate is filtered off, washed with fresh hexane and dried for 2 hours at 50° (0.1 mm.) to yield 2-(4-bromobutyl)-1H-benz[de] isoquinoline-1,3 (2H)-dione. An analytically pure sample is prepared by dissolving the above product in hot 95% ethanol and recrystallizing by allowing the solution to cool to 25°. The resulting precipitate is dried for two hours at 50° (0.1 mm.) to yield pure 2-(4-bromobutyl)-1H-benz[de] isoquinoline-1,3 (2H)-dione, m.p. 113°–115°.

b. 2-[4-(4-Phenyl-1-piperidinyl)butyl]-1H-benz[de] isoquinoline-1,3 (2H)-dione, hydrochloride (1:1)

10 g. (0.03 mole) of the product from part (a), 5.0 g. (0.031 mole) of 4-phenylpiperidine and 15 g. of sodium carbonate are combined in 200 ml. of toluene and refluxed for 24 hours. After cooling to 25°, 100 ml. of water is added and the resulting mixture is shaken. Some insoluble gum is filtered off and the two layers of the filtrate are separated. The organic layer is washed with water and shaken with excess 10% aqueous HCl. The precipitate that separates from both layers is filtered off and recrystallized by dissolving in hot ethanol, diluting with an equal volume of water and cooling. The resulting crystals are filtered off and dried for ten hours at 80° (0.1 mm.) to yield 11.3 g. of 2-[4-(4-phenyl-1-piperidinyl)butyl]-1H-benz[de]isoquinoline-1,3 (2H)-dione, hydrochloride (1:1); m.p. 226°–228°.

c. 2-[4-(4-Phenyl-1-piperidinyl)butyl]-2,3-dihydro-3-hydroxy-1H-benz[de]isoquinolin-1-one The hydrochloride salt product from part (b) is treated according to the procedure of example 38(b) to yield the titled compound.

EXAMPLE 42

2-[6-(4-Phenyl-1-piperidinyl)hexyl]-2,3-dihydro-3-hydroxy-1H-benz[de]isoquinolin-1-one Following the procedure of example 4 but substituting 4-phenylpiperidine for the 4-phenyl-1,2,3,6-tetrahydropyridine in part (b), one obtains the titled compound.

EXAMPLE 43

2-[5-(4-Phenyl-1-piperidinyl)pentyl]-2,3-dihydro-3-hydroxy-1H-benz[de]isoquinolin-1-one Following the procedure of example 5 but substituting 4-phenylpiperidine for the 4-phenyl-1,2,3,6-tetrahydropyridine in part (b), one obtains the titled compound.

EXAMPLE 44

2-[2-[4-(3-Phenylpropyl)-1-piperidinyl]ethyl]-2,3-dihydro-3-hydroxy-1H-benz[de]isoquinolin-1-one a. 2-[2-[4-(3-Phenylpropyl)-1-piperidinyl]ethyl]-1H-benz[de]isoquinoline-1,3(2H)-dione, hydrochloride (1:1)

10 g. (0.025 mole) of the ester from Example 1(b), 5.35 g. (0.026 mole) of 4-(3-phenylpropyl)piperidine and 3.26 g. (0.024 mole) of diisopropylethylamine are refluxed in 500 ml. of toluene for three hours. The reaction mixture is cooled, shaken with 10% KOH, washed with water, and filtered. Shaking the toluene layer with the 10% HCl precipitates crude product which is then filtered from the two phases and washed with toluene and water. Recrystallization of the filter cake twice from absolute ethanol yields 7.0 g. of pure 2-[2-[4-(3-phenylpropyl)-1-piperidinyl]ethyl]-1H-benz[de]isoquinoline-1,3(2H)-dione, hydrochloride (1:1); m.p. 212°–213° (dec.).

b. 2-[2-[4-(3-Phenylpropyl)-1-piperidinyl]ethyl]-2,3-dihydro-3-hydroxy-1H-benz[de]isoquinolin-1-one The hydrochloride salt product from part (a) is treated according to the procedure of example 38(b) to yield the titled compound.

EXAMPLES 45–65

Following the procedure of example 38 but substituting for (4-phenylmethyl)piperidine an equivalent amount of one of the following:

2-phenylpiperidine
3-phenylpiperidine
4-(2-phenylethyl)piperidine
3-(3-phenylpropyl)piperidine
4-(4-phenylbutyl)piperidine
3-(phenylmethyl)piperidine
2-(2-phenylethyl)piperidine
4-(4-chlorophenyl)piperidine
4-(4-fluorophenyl)piperidine
4-(3-trifluoromethylphenyl)piperidine
4-(3,4-dichlorophenyl)piperidine
4-(2-bromophenyl)piperidine
4-(3-methylphenyl)piperidine
4-(2-ethoxyphenyl)piperidine
4-(4-nitrophenyl)piperidine
3-(4-chlorophenyl)piperidine
2-(4-nitrophenyl)piperidine
4-[(4-chlorophenyl)methyl]piperidine
4-[2-(4-fluorophenyl) ethyl]piperidine
4-[3-(3-ethylphenyl)propyl]piperidine
3-[(2-bromophenyl)methyl]piperidine one obtains:

2-[2-(2-phenyl-1-piperidinyl)ethyl]-2,3-dihydro-3-hydroxy-1H-benz[de]isoquinolin-1-one;
2-[2-(3-phenyl-1-piperidinyl)ethyl]-2,3-dihydro-3-hydroxy-1H-benz[de]isoquinolin-1-one;
2-[2-[4-(2-phenylethyl)-1-piperidinyl]ethyl]-2,3-dihydro-3-hydroxy-1H-benz[de]isoquinolin-1-one;
2-[2-[3-(3-phenylpropyl)-1-piperidinyl]ethyl]-2,3-dihydro-3-hydroxy-1H-benz[de]isoquinolin-1-one;
2-[2-[4-(4-phenylbutyl)-1-piperidinyl]ethyl]-2,3-dihydro-3-hydroxy-1H-benz[de]isoquinolin-1-one;
2-[2-[3-(phenylmethyl)-1-piperidinyl]ethyl]-2,3-dihydro-3-hydroxy-1H-benz[de]isoquinolin-1-one;
2-[2-(2-phenylethyl)-1-piperidinyl]ethyl]-2,3-dihydro-3-hydroxy-1H-benz[de]isoquinolin-1-one;
2-[2-[4-(4-chlorophenyl)-1-piperidinyl]ethyl]-2,3-dihydro-3-hydroxy-1H-benz[de]isoquinolin-1-one;
2-[2-[4-(4-fluorophenyl)-1-piperidinyl]ethyl]-2,3-dihydro-3-hydroxy-1H-benz[de]isoquinolin-1-one;
2-[2-[4-(3-trifluoromethylphenyl)-1-piperidinyl]ethyl]-2,3-dihydro-3-hydroxy-1H-benz-[de]isoquinolin-1-one;
2-[2-[4-(4-nitrophenyl)-1-piperidinyl]ethyl]-2,3-dihydro-3-hydroxy-1H-benz[de]isoquinolin-1-one;
2-[2-[4-(2-bromophenyl)-1-piperidinyl]ethyl]-2,3-dihydro-3-hydroxy-1H-benz[de]isoquinolin-1-one;
2-[2-[4-(3-methylphenyl)-1-piperidinyl]ethyl]-2,3-dihydro-3-hydroxy-1H-benz[de]isoquinolin-1-one;
2-[2-[4-(2-ethoxyphenyl)-1-piperidinyl]ethyl]-2,3-dihydro-3-hydroxy-1H-benz[de]isoquinolin-1-one;
2-[2-[4-(4-nitrophenyl)-1-piperidinyl]ethyl]-2,3-dihydro-3-hydroxy-1H-benz[de]isoquinolin-1-one;

2-[2-[3-(4-chlorophenyl)-1-piperidinyl]ethyl]-2,3-dihydro- 3-hydroxy-1H-benz[de] isoquinolin-1-one;

2-[2-[2-(4-nitrophenyl)-1-piperidinyl]ethyl]-2,3-dihydro-3-hydroxy-1H-benz[de] isoquinolin-1-one;

2-[2-[4-[(4-chlorophenyl)methyl]-1-piperidinyl]ethyl]-2,3-dihydro-3-hydroxy-1H-benz[de] isoquinolin-1-one;

2-[2-[4-[2-(4-fluorophenyl)ethyl]-1-piperidinyl]ethyl]-2,3-dihydro-3-hydroxy-1H-benz-[de]isoquinolin-1-one;

2-[2-[4-[3-(3-ethylphenyl)propyl]-1-piperidinyl-]ethyl-2,3-dihydro-3-hydroxy-1H-benz-[de]isoquinolin-1-one;

and 2-[2-[3-[(2-bromophenyl)methyl]-1-piperidinyl]ethyl]-2,3-dihydro-3-hydroxy-1H-benz[de]isoquinolin-1-one; respectively.

Similarly, by employing the piperidine reactants of examples 38 and 44 to 65 within the procedures of examples 40 to 43, other compounds within the scope of invention are obtained.

Also, by employing the alkanolamines of examples 29 to 37 within the procedures of examples 38, 39, and 44 to 65, other compounds within the scope of the invention are obtained.

EXAMPLE 66

2-[2-(4-Hydroxy-4-phenyl-1-piperidinyl)ethyl]-2,3-dihydro-3-hydroxy-1H-benz[de]isoquinolin-1-one a. 2-[2-(4-Hydroxy-4-phenyl-1-piperidinyl)ethyl-1H-benz[de]isoquinoline-1,3 (2H)-dione 10 g. (0.025 mole) of the ester from example 1(b), 4.9 g. (0.028 mole) of (4-hydroxy-4-phenyl)piperidine, and 3.26 g. (0.025 mole) of diisopropylethylamine in 200 ml. of toluene are refluxed for 3.5 hours. The toluene is evaporated and the residue is taken up in chloroform, washed with 10% KOH, filtered, and washed with water (all aqueous layers are backwashed). The chloroform layers are combined and warmed with activated carbon, filtered, and evaporated. The residue is recrystallized from ethanol and toluene to yield 2.2 g. of 2-[2-(4-hydroxy-4-phenyl-1-piperidinyl)ethyl]-1H-benz[de]isoquinoline-1,3 (2H)-dione; m.p. 177°–179°.

b. 2-[2-(4-Hydroxy-4-phenyl-1-piperidinyl)ethyl]-2,3-dihydro-3-hydroxy-1H-benz[de]isoquinolin-1-one The product from part (a) is reacted with sodium borohydride as taught in either example 1 or 38 to yield the titled compound.

EXAMPLE 67

2-[2-(4-Hydroxy-4-phenyl-1-piperidinyl)propyl]-2,3-dihydro-3-hydroxy-1H-benz[de]isoquinolin-1-one Following the procedure of example 2 but substituting (4-hydroxy-4-phenyl)piperidine for the 4-phenyl 1,2,3,6-tetrahydropyridine in part (b), one obtains the titled compound.

EXAMPLE 68

2-[4-(4-Hydroxy-4-phenyl-1-piperidinyl)butyl]-2,3-dihydro-3-hydroxy-1H-benz[de] isoquinolin-1-one a. 2-[4-(4-Hydroxy-4-phenyl-1-piperidinyl)butyl]-1H-benz[de]isoquinoline-1,3 (2H)-dione 10 g. (0.03 moles) of 2-(4-bromobutyl)-1H-benz-[de]isoquinoline-1,3 (2H)-dione from example 41 (a) and 5.4 g. (0.03 moles) of 4-hydroxy-4-phenylpiperidine are refluxed over excess (10 g.) anhydrous sodium carbonate in 150 ml. of n-butanol overnight. The solvent is evaporated and the residue is taken up in water and chloroform. The chloroform layer is washed twice with water, dried ($Na_2SO_4$), and evaporated. The residue is recrystallized first from ethanol and then from toluene to yield 6.72 g. of 2-[4-(4-hydroxy-4-phenyl-1-piperidinyl)butyl]-1H-benz[de]isoquinoline-1,3 (2H)-dione; m.p. 138°–139°.

b. 2-[4-[4-Hydroxy-4-phenyl-1-piperidinyl)butyl]-2,3-dihydro-3-hydroxy-1H-benz[de]isoquinolin-1-one The product from part (a) is reacted with sodium borohydride as taught in either example 1 or 38 to yield the titled compound.

EXAMPLE 69

2-[6-(4-Hydroxy-4-phenyl-1-piperidinyl)hexyl]-2,3-dihydro-3-hydroxy-1H-benz[de]isoquinolin-1-one Following the procedure of example 4 but substituting 4-hydroxy-4-phenylpiperidine for the 4-phenyl-1,2,3,6-tetrahydropyridine in part (b), one obtains the titled compound.

EXAMPLE 70

2-[5-(4-Hydroxy-4-phenyl-1-piperidinyl)pentyl]-2,3-dihydro-3-hydroxy-1H-benz[de]isoquinolin-1-one Following the procedure of example 5 but substituting 4-hydroxy-4-phenylpiperidine for the 4-phenyl-1,2,3,6-tetrahydropyridine in part (b), one obtains the titled compound.

EXAMPLES 71–87

Following the procedure of example 66 but substituting for the (4-hydroxy-4-phenyl)piperidine one of the following:

(3-hydroxy-3-phenyl)piperidine
[4-hydroxy-4-(4-chlorophenyl)]piperidine
[4-hydroxy-4-(3-trifluoromethylphenyl)]piperidine
[4-hydroxy-4-(3-ethylphenyl)]piperidine
[4-hydroxy-4-(2-methoxyphenyl)]piperidine
[3-hydroxy-3-(4-bromophenvl)]piperidine
[4-hydroxy-4-(3,4-dichlorophenyl)]piperidine
[4-hydroxy-4-(4-nitrophenyl)]piperidine
[4-hydroxy-4-(phenylmethyl)]piperidine
[4-hydroxy-4-(2-phenylethyl)]piperidine
[4-hydroxy-4-(3-phenylpropyl)]piperidine
[3-hydroxy-3-[(4-chlorophenyl)methyl]]piperidine
[4-hydroxy-4-[(3-methoxyphenyl)methyl]]piperidine
[4-hydroxy-4-[(4-nitrophenyl)methyl]]piperidine
[4-hydroxy-4-[(3,4-dichlorophenyl)methyl]]piperidine
[4-hydroxy-4-[2-(4-fluorophenyl)ethyl]]piperidine
[4-hydroxy-4-[3-(4-methylphenyl)propyl]]piperidine one obtains:

2-[2-(3-hydroxy-3-phenyl-1-piperidinyl)ethyl]-2,3-dihydro-3-hydroxy-1H-benz[de]isoquinolin-1-one;

2-[2-[4-hydroxy-4-(4-chlorophenyl)-1-piperidinyl]ethyl]-2,3-dihydro-3-hydroxy-1H-benz-[de]isoquinolin-1-one;

2-[2-[4-hydroxy-4-(3-trifluoromethylphenyl)-1-piperidinyl]ethyl]-2,3-dihydro-3-hydroxy-1H-benz[de]isoquinolin-1-one;

2-[2-[4-hydroxy-4-(3-ethylphenyl)-1-piperidinyl]ethyl]-2,3-dihydro-3-hydroxy-1H-benz-[de]isoquinolin-1-one;

2-[2-[4-hydroxy-4-(2-methoxyphenyl)-1-piperidinyl-]ethyl]-2,3-dihydro-3-hydroxy-1H-benz-[de]isoquinolin-1-one;
2-[2-[3-hydroxy-3-(4-bromophenyl)-1-piperidinyl-]ethyl]-2,3-dihydro-3-hydroxy-1H-benz-[de]isoquinolin-1-one;
2-[2-[4-hydroxy-4-(3,4-dichlorophenyl)-1-piperidinyl]ethyl]-2,3-dihydro-3-hydroxy-1H-benz[de]isoquinolin-1-one;
2-[2-[4-hydroxy-4-(4-nitrophenyl)-1-piperidinyl]ethyl]-2,3-dihydro-3-hydroxy-1H-benz-[de]isoquinolin-1-one;
2-[2-[4-hydroxy-4-(phenylmethyl)-1-piperidinyl]ethyl]-2,3-dihydro-3-hydroxy-1H-benz-[de]isoquinolin-1-one;
2-[2-[4-hydroxy-4-(2-phenylethyl)-1-piperidinyl]ethyl]-2,3-dihydro-3-hydroxy-1H-benz-[de]isoquinolin-1-one;
2-[-2-[4-hydroxy-4-(3-phenylpropyl)-1-piperidinyl-]ethhyl]-2,3-dihydro-3-hydroxy-1H-benz-[de]isoquinolin-1-one;
2-[2-[3-hydroxy-3-[(4-chlorophenyl)methyl]-1-piperidinyl]ethyl]-2,3-dihydro-3-hydroxy-1H-benz[de]isoquinolin-1-one;
2-[2-[4-hydroxy-4-[(3-methoxyphenyl)methyl]-1-piperidinyl]ethyl-2,3-dihydro-3-hydroxy-1H-benz-[de]isoquinolin-1-one;
2-[2-[4-hydroxy-4-[(4-nitrophenyl)methyl]-1-piperidinyl]ethyl]-2,3-dihydro-3-hydroxy-1H-benz[de]isoquinolin-1-one;
2-[2-[4-hydroxy-4-[(3,4-dichlorophenyl)methyl]-1-piperidinyl]ethyl]-2,3-dihydro-3-hydroxy-1H-benz[de]isoquinolin-1-one;
2-[2-[4-hydroxy-4-[2-(4-fluorophenyl)ethyl]-1-piperidinyl]ethyl]-2,3-dihydro-3-hydroxy-1H-benz[de]isoquinolin-1-one;
and 2-[2-[4-hydroxy-4-[3-(4-methylphenyl)propyl]-1-piperidinyl]ethyl]-2,3-dihydro-3-hydroxy-1H-benz[de]isoquinolin-1-one;

respectively.

Similarly, the hydroxyphenylpiperidine reactants of examples 71 to 87 can be employed in the procedures of examples 67 to 70 to obtain other compounds within the scope of this invention.

Also, by employing the alkanolamines of examples 29 to 37 within the procedures of examples 66 and 71 to 87, other compounds within the scope of this invention are obtained.

EXAMPLE 88

2-[2-(4-Phenyl-1-piperazinyl)ethyl]-2,3-dihydro-3-hydroxy-1H-benz[de]isoquinolin-1-one a. 2-[2-(4-Phenyl-1-piperazinyl)ethyl]-1H-benz-[de]isoquinoline-1,3(2H)-dione, hydrochloride (1:2)

10 g. (0.025 mole) of the ester from example 1 (b), 4.3 g. (0.026 mole) of N-phenylpiperazine, and 3.27 g. (0.025 mole) of diisopropylethylamine are refluxed in 500 ml. of toluene for four hours. The reaction mixture is then shaken with 5% NaOH, filtered, washed with water (all aqueous layers are backwashed with toluene), and shaken with 10% HCl. The precipitate that forms is filtered and washed with water and toluene. Recrystallization from water/ethanol yields 3.0 g. of 2-[2-(4-phenyl-1-piperazinyl)ethyl]-1H-benz-[de]isoquinoline-1,3(2H)-dione, hydrochloride (1:2); m.p. 286°-287° (dec.).

b. 2-[2-(4-Phenyl-1-piperzinyl)ethyl]-2,3-dihydro-3-hydroxy-1H-benz[de]isoquinoline-1-one 10 g. (0.021 moles) of the hydrochloride salt product of part (a) is dissolved in chloroform and washed with 10% KOH and twice with water. The chloroform is evaporated and the residue is dissolved in a solution of 100 ml. of dioxane and 100 ml. of ethanol. 7.95 g. (0.021 moles) of sodium borohydride is added and the mixture is stirred overnight at 25°. 50 ml. of water is added, the mixture is stirred for one hour, and the solvent mixture is evaporated to dryness. The residue is taken up in chloroform and washed with 10% KOH, twice with water, dried ($Na_2SO_4$), and evaporated. The residue is recrystallized from ethanol to yield 5.0 g. of 2-[2-(4-phenyl-1-piperazinyl)ethyl]-2,3-dihydro-3-hydroxy-1H-benz[de]isoquinolin-1-one; m.p. 179°-180° (dec.).

EXAMPLE 89

2-[3-(4-Phenyl-1-piperazinyl)propyl]-2,3-dihydro-3-hydroxy-1H-benz[de]isoquinolin-1-one Following the procedure of example 88 but employing the ester from example 2(a), one obtains the titled compound.

Similarly, by following the procedure of example 88 but employing the alkanolamines of example 29 to 37, other compounds within the scope of this invention are obtained.

EXAMPLE 90

2-[4-(4-Phenyl-1-piperazinyl)butyl]-2,3-dihydro-3-hydroxy-1H-benz[de]isoquinolin-1-one a. 2-[4-(4-Phenyl-1-piperazinyl)butyl]-1H-benz-[de]isoquinoline-1,3(2H)-dione, hydrochloride (1:1)

9.0 g. (0.027 mole) of 2-(4-bromobutyl)-1H-benz-[de]isoquinoline-1,3(2H)-dione from example 41(a) and 4.5 g. (0.027 mole) of N-phenylpiperazine are refluxed for two days over excess anhydrous sodium carbonate. The cooled reaction mixture is washed with water and the water layer is backwashed with toluene. The combined organic layers are washed with water twice and shaken with 10% HCl for one hour. The resulting precipitate is filtered from the two phases, washed with water and toluene, and dried in vacuo at 100° for one hour to yield 9.33 g. of 2-[4-(4-phenyl-1-piperazinyl)butyl]-1H-benz[de]isoquinoline-1,3(2H)-dione, hydrochloride (1:1); m.p. 265°-267° (dec.).

b. 2-[4-(4-Phenyl-1-piperazinyl)butyl]-2,3-dihydro-3-hydroxy-1H-benz[de]isoquinolin-1-one Treating the hydrochloride salt product from part (a) according to the procedure of example 88(b), one obtains the titled compound.

EXAMPLE 91

2-[2-[4-(4-Methoxyphenyl)-1-piperazinyl]ethyl]-2,3-dihydro-3-hydroxy-1H-benz[de]isoquinolin-1-one a. 2-[2-[4-(4-Methoxyphenyl)-1-piperazinyl]ethyl]-1H-benz[de]isoquinoline-1,3(2H)-dione, hydrochloride (1:2)

Following the procedure of example 88(a) but substituting 5.1 g. (0.026 mole) of 1-(p-methoxyphenyl)piperazine for the N-phenylpiperazine, one obtains 8.0 g. of 2-[2-[4-(4-methoxyphenyl)-1-piperazinyl]ethyl]-1H-benz[de]isoquinoline-1,3(2H)-dione, hydrochloride (1:2); m.p. 270°-271° (dec.).

b. 2-[2-[4-(4-Methoxyphenyl)-1-piperazinyl]ethyl]-2,3-dihydro-3-hydroxy-1H-benz[de]isoquinolin-1-one Treating the hydrochloride salt product from part (a) according to the procedure of example 88(b), one obtains the titled compound.

EXAMPLE 92

2-[2-[4-(2-Methoxyphenyl)-1-piperazinyl]ethyl]-2,3-dihydro-3-hydroxy-1H-benz[de]isoquinolin-1-one a. 2-[2-[4-(2-Methoxyphenyl)-1-piperazinyl]ethyl]-1H-benz[de]-isoquinoline-1,3(2H)-dione, hydrochloride (1:2)

Following the procedure of example 88(a) but substituting 5.1 g. (0.026 mole) of 1-(o-methoxyphenyl)piperazine for the N-phenylpiperazine, one obtains 2.9 g. of 2-[2-[4-(2-methoxyphenyl)-1-piperazinyl]ethyl]-1H-benz[de]isoquinoline-1,3(2H)-dione, hydrochloride (1:2); m.p. 284° (dec.).

b. 2-[2-[4-(2-Methoxyphenyl)-1-piperazinyl]ethyl]-2,3-dihydro-3-hydroxy-1H-benz[de]isoquinolin-1-one Treating the hydrochloride salt product from part (a) according to the procedure of example 88(b), one obtains the titled compound.

EXAMPLE 93

2-[2-[4-(4-Chlorophenyl)-1-piperazinyl]ethyl]-2,3-dihydro-3-hydroxy-1H-benz[de]isoquinolin-1-one a. 2-[2-[4-(4-Chlorophenyl)-1-piperazinyl]ethyl]-1H-benz[de]isoquinoline-1,3(2H)-dione, hydrochloride (1:1)

Following the procedure of example 88(a) but substituting 5.2 g. (0.026 mole) of 1-(p-chlorophenyl)piperazine for the N-phenylpiperazine, one obtains 3.0 g. of 2-[2-[4-(4-chlorophenyl)-1-piperazinyl]ethyl]-1H-benz[de]isoquinoline-1,3(2H)-dione, hydrochloride (1:1); m.p. 286°–287° (dec.).

b. 2-[2-[4-(4-Chlorophenyl)-1-piperazinyl]ethyl]-2,3-dihydro-3-hydroxy-1H-benz[de]isoquinolin-1-one Treating the hydrochloride salt product from part (a) according to the procedure of example 88(b), one obtains the titled compound.

EXAMPLE 94

2-[2-[4-(2-Chlorophenyl)-1-piperazinyl]ethyl]-2,3-dihydro-3-hydroxy-1H-benz[de]isoquinolin-1-one a. 2-[2-[4-(2-Chlorophenyl)-1-piperazinyl]ethyl]-1H-benz[de]isoquinoline-1,3(2H)-dione Following the procedure of example 88(a) but substituting 5.2 g. (0.026 mole) of 1-(o-chlorophenyl)piperazine for the N-phenylpiperazine, one obtains the hydrochloride salt of 2-[2-[4-(2-chlorophenyl)-1-piperazinyl]ethyl]-1H-benz[de]isoquinoline-1,3(2H)-dione. This salt is neutralized with aqueous sodium hydroxide and extracted with chloroform. The chloroform solution is dried ($Na_2SO_4$), concentrated to 200 ml. and allowed to stand open to the air. The product slowly crystallizes and is removed by filtration. Drying at 50° (60 mm.) overnight yields 4 g. of 2-[2-[4-(2-chlorophenyl)-1-piperazinyl]ethyl]-1H-benz-[de]isoquinoline-1,3(2H)-dione; m.p. 213°–214°.

b. 2-[2-[4-(2-Chlorophenyl)-1-piperazinyl]ethyl]-2,3-dihydro-3-hydroxy-1H-benz[de]isoquinolin-1-one Treating the product from part (a) with sodium borohydride according to the procedure of example 88(b), one obtains the titled compound.

EXAMPLE 95

2-[2-[4-[3-(Trifluoromethyl)phenyl]-1-piperazinyl]ethyl]-2,3-dihydro-3-hydroxy-1H-benz[de]isoquinolin-1-one a. 2-[2-[4-[3-(Trifluoromethyl)phenyl]-1-piperazinyl]ethyl]-1H-benz[de]isoquinoline-1,3(2H)-dione, hydrochloride (1:1)

Following the procedure of example 88(a) but substituting 6.1 g. (0.026 mole) of 1-[3-(trifluoromethyl)-phenyl]piperazine for the N-phenylpiperazine, one obtains 6.53 g. of 2-[2-[4-[3-(trifluoromethyl)phenyl]-1-piperazinyl]ethyl]-1H-benz[de]isoquinoline-1,3(2H)-dione, hydrochloride (1:1); m.p. 276°–277° (dec.).

b. 2-[2-[4-[3-(Trifluoromethyl)phenyl]-1-piperazinyl]ethyl]-2,3-dihydro-3-hydroxy-1H-benz-[de]isoquinolin-1-one Treating the hydrochloride salt product from part (a) according to the procedure of example 88(b), one obtains the titled compound.

EXAMPLE 96

2-[2-[4-(4-Fluorophenyl)-1-piperazinyl]ethyl]-2,3-dihydro-3-hydroxy-1H-benz[de]isoquinolin-1-one a. 2-[2-[4-(4-Fluorophenyl)-1-piperazinyl]ethyl]-1H-benz[de]isoquinoline-1,3(2H)-dione, hydrochloride (1:1)

Following the procedure of example 88(a) but substituting 4.8 g. (0.026 mole) of 1-(p-fluorophenyl)piperazine for the N-phenylpiperazine, one obtains 6.1 g. of 2-[2-[4-(4-fluorophenyl)-1-piperazinyl]ethyl]-1H-benz[de]isoquinoline-1,3(2H)-dione, hydrochloride (1:1); m.p. 309°–310° (dec.).

b. 2-[2-[4-(4-Fluorophenyl)-1-piperazinyl]ethyl]-2,3-dihydro-3-hydroxy-1H-benz[de]isoquinolin-1-one Treating the hydrochloride salt product from part (a) according to the procedure of example 88(b), one obtains the titled compound.

EXAMPLE 97

2-[2-[4-(Phenylmethyl)-1-piperazinyl]ethyl]-2,3-dihydro-3-hydroxy-1H-benz[de]isoquinolin-1-one a. 2-[2-[4-(Phenylmethyl)-1-piperazinyl]ethyl]-1H-benz[de]isoquinoline-1,3(2H)-dione, hydrochloride (1:2)

Following the procedure of example 88(a) but substituting 4.7 g. (0.026 mole) of 1-(phenylmethyl)piperazine for the N-phenylpiperazine, one obtains 10.8 g. of 2-[2-[4-(phenylmethyl)-1-piperazinyl]ethyl]-1H-benz-[de]isoquinoline-1,3(2H)-dione, hydrochloride (1:2); preliminary melting at 278°–281° and final melting with decomposition at 284°.

b. 2-[2-[4-(Phenylmethyl)-1-piperazinyl]ethyl]-2,3-dihydro-3-hydroxy-1H-benz[de]isoquinolin-1-one Treating the hydrochloride salt product from part (a) according to the procedure of example 88(b), one obtains the titled compound.

EXAMPLES 98–111

Following the procedure of example 88 but substituting for the N-phenylpiperazine in part (a) an equivalent amount of one of the following:

1-(2-phenylethyl)piperazine
1-(3-phenylpropyl)piperazine
1-(4-phenylbutyl)piperazine
1-(3,5-dichlorophenyl)piperazine
1-(4-ethylphenyl)piperazine
1-(4-nitrophenyl)piperazine
1-(2-propylthiophenyl)piperazine
1-(3-trifluoromethyl-4-chlorophenyl)piperazine
1-(3-trifluoromethyl-4-methylphenyl)piperazine
1-[(4-bromophenyl)methyl]piperazine
1-[2-(4-chlorophenyl)ethyl]piperazine
1-[(3-trifluoromethylphenyl)methyl]piperazine
1-[3-(4-methylphenyl)propyl]piperazine
1-[(3,5-dimethoxyphenyl)methyl]piperazine one obtains:

2-[2-[4-(2-phenylethyl)-1-piperazinyl]ethyl]-2,3-dihydro-3-hydroxy-1H-benz[de]isoquinolin-1-one;
2-[2-[4-(3-phenylpropyl)-1-piperazinyl]ethyl]-2,3-dihydro-3-hydroxy-1H-benz[de]isoquinolin-1-one;
2-[2-[4-(4-phenylbutyl)-1-piperazinyl]ethyl]-2,3-dihydro-3-hydroxy-1H-benz[de]isoquinolin-1-one;
2-[2-[4-(3,5-dichlorophenyl)-1-piperazinyl]ethyl]-2,3-dihydro-3-hydroxy-1H-benz[de]isoquinolin-1-one;
2-[2-[4-(4-ethylphenyl)-1-piperazinyl]ethyl]-2,3-dihydro-3-hydroxy-1H-benz[de]isoquinolin-1-one;
2-[2-[4-(4-nitrophenyl)-1-piperazinyl]ethyl]-2,3-dihydro-3-hydroxy-1H-benz[de]isoquinolin-1-one;
2-[2-[4-(2-propylthiophenyl)-1-piperazinyl]ethyl]-2,3-dihydro-3-hydroxy-1H-benz[de]isoquinolin-1-one;
2-[2-[4-(3-trifluoromethyl-4-chlorophenyl)-1-piperazinyl]ethyl]-2,3-dihydro-3-hydroxy-1H-benz[de]isoquinolin-1-one;
2-[2-[4-(3-trifluoromethyl-4-methylphenyl)-1-piperazinyl]ethyl]-2,3-dihydro-3-hydroxy-1H-benz[de]isoquinolin-1-one;
2-[2-[4-[(4-bromophenyl)methyl]-1-piperazinyl]ethyl]-2,3-dihydro-3-hydroxy-1H-benz-[de]isoquinolin-1-one;
2-[2-[4-[2-(4-chlorophenyl)ethvl]-1-piperazinyl]ethyl]-2,3-dihydro-3-hydroxy-1H-benz-[de]isoquinolin-1-one;
2-[2-[4-[(3-trifluoromethylphenyl)methyl]-1-piperazinyl]-2,3-dihydro-3-hydroxy-1H-benz-[de]isoquinolin-1-one;
2-[2-[4-[3-(4-methylphenyl)propyl]-1-piperazinyl]-2,3-dihydro-3-hvdroxy-1H-benz[de]isoquinolin-1-one;
and 2-[2-[4-[(3,5-dimethoxyphenyl)methyl]-1-piperazinyl]-ethyl]-2,3-dihydro-3-hydroxy-1H-benz[de]isoquinolin-1-one;

respectively.

Similarly, by employing the piperazine reactants of examples 91 to 111 within the procedures of examples 89 and 90, other compounds within the scope of the invention are obtained.

EXAMPLE 112

2-[2-[4-(2-Pyridinyl)-1-piperazinyl]ethyl]-2,3-dihydro-3-hydroxy-1H-benz[de]isoquinolin-1-one a. 2-[2-[4-(2-Pyridinyl)-1-piperazinyl]ethyl]-1H-benz-[de]-isoquinoline-1,3(2H)-dione, hydrochloride (1:2)

10 g. (0.025 moles) of the ester from example 1(b), 4.1 g. (0.025 moles) of 1-(2-pyridinyl)piperazine and 3.27 g. (0.0253 moles) of diisopropylethylamine are refluxed in 300 ml. of toluene for 3.5 hours. The toluene is evaporated and the residue is dissolved in chloroform and washed with water (all aqueous layers are backwashed). The chloroform is evaporated and the residue is recrystallized from chloroform/ethanol to yield 2-[2-[4-(2-pyridyl)-1-piperazinyl]ethyl]-1H-benz[de]isoquinoline-1,3(2H)-dione; m.p. 188°–190°.

This free base is dissolved in hot chloroform/ethanol and treated with excess alcoholic HCl causing the salt to precipitate. Recrystallization of this crude salt from methanol and methanol/ether followed by drying at 80° under a vacuum yields 4.0 g. of pure 2-[2-[4-(2-pyridinyl)-1-piperazinyl]ethyl]-1H-benz[de]isoquinoline-1,3(2H)-dione, hydrochloride (1:2); m.p. 283°–284° (dec.).

b. 2-[2-[4-(2-Pyridinyl)-1-piperazinyl]ethyl]-2,3-dihydro-3-hydroxy-1H-benz[de]isoquinolin-1-one 14.0 g. (0.0363 moles) of the hydrochloride salt product from part (a) is converted to the free base by dissolving in chloroform, washing with NaOH and water, drying ($NaSO_4$), and evaporating the chloroform. This material is dissolved in 200 ml. of dioxane and 16 g. (0.0443 moles) of sodium borohydride and 50 ml. of ethanol are added. The solution is stirred overnight, the solvent is evaporated, and the residue is taken up in chloroform. The chloroform solution is washed with 5% KOH, twice with water, dried ($Na_2SO_4$), and the solvent evaporated. Recrystallization from ethanol yields 2.98 g. of 2-[2-[4-(2-pyridinyl)-1-piperazinyl]ethyl]-2,3-dihydro-3-hydroxy-1H-benz[de]isoquinolin-1-one; m.p. 174°–175°.

EXAMPLE 113

2-[3-[4-(2-Pyridinyl)-1-piperazinyl]propyl]-2,3-dihydro-3-hydroxy-1H-benz[de]isoquinolin-1-one Following the procedure of example 112 but employing the ester from example 2(a), one obtains the titled compound.

Similarly, by following the procedure of example 112 but employing the alkanolamines of examples 29 to 37, other compounds within the scope of this invention are obtained.

EXAMPLE 114

2-[4-[4-(2-Pyridinyl)-1-piperazinyl]butyl]-2,3-dihydro-3-hydroxy-1H-benz[de]isoquinolin-1-one a. 2-[4-[4-(2-Pyridinyl)-1-piperazinyl]butyl]-1H-benz-[de]isoquinoline-1,3(2H)-dione, hydrochloride (1:2)

9.0 g. (0.0271 mole) of 2-(4-bromobutyl)-1H-benz-[de]isoquinoline-1,3(2H)-dione from example 41 (a), 4.73 g. (0.0276 mole) of 1-(2-pyridinyl)piperazine, and excess sodium carbonate are refluxed in 200 ml. of benzene for two days. The sodium carbonate is filtered off and washed with hot chloroform. The organic portions are combined and evaporated and the residue is dissolved in toluene and extracted with 10% HCl (twice). The combined acid portions are then washed with toluene and neutralized with KOH pellets. The resulting precipitate is extracted into chloroform, washed with water (twice), dried ($Na_2SO_4$), and evaporated. The residue is recrystallized from ethanol to yield 11.74 g. of 2-[4-[4-(2-pyridinyl)-1-piperazinyl]-butyl]-1H-benz[de]isoquinoline-1,3(2H)-dione; m.p. 150°–152°.

This free base is dissolved in dioxane and treated with 5N HCl in dioxane to precipitate 9.4 g. of 2-[4-[4-(2- pyridinyl)-1-piperazinyl]butyl]-1H-benz[de]isoquinoline-1,3-(2H)-dione, hydrochloride (1:2); m.p. 280°–282°.

b. 2-[4-[4-(2-Pyridinyl)-1-piperazinyl]butyl]-2,3-dihydro-3-hydroxy-1H-benz[de]isoquinolin-1-one Treating the hydrochloride salt product from part (a) according to the procedure of example 112(b), one obtains the titled compound.

EXAMPLES 115-146

Following the procedure of example 112 but substituting for the 1-(2-pyridinyl)piperazine the compounds shown in Col. I one obtains the products shown in Col. II wherein Het represents the radical shown below.

| Col. I | Col. II |
|---|---|
| 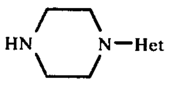 | 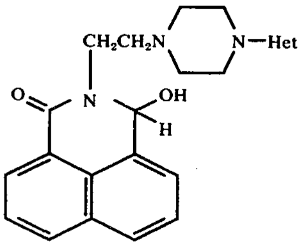 |
| Ex. | Het |
| 115 | 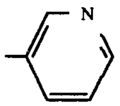 |
| 116 | 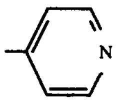 |
| 117 | 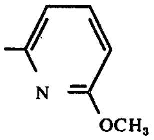 |
| 118 | 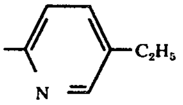 |
| 119 | 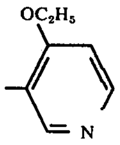 |
| 120 | 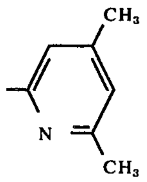 |
| 121 | 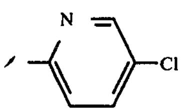 |

-continued

| Col. I | Col. II |
|---|---|
| 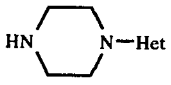 | 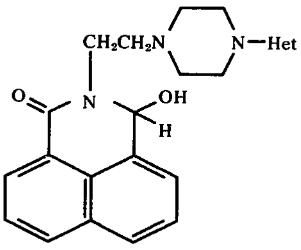 |
| Ex. | Het |
| 122 | 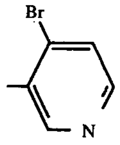 |
| 123 | 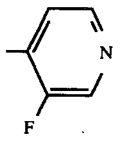 |
| 124 | 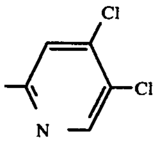 |
| 125 | 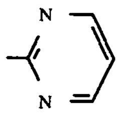 |
| 126 | 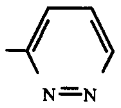 |
| 127 | 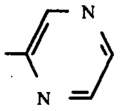 |
| 128 | 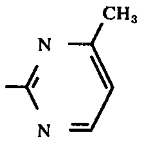 |
| 129 | 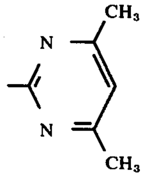 |
| 130 | 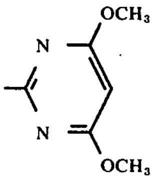 |

-continued
| Col. I | Col. II |
|---|---|
| 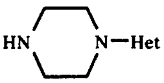 | 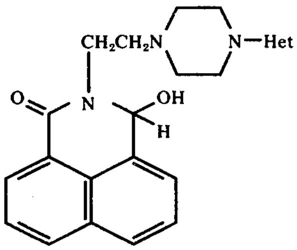 |
| Ex. | Het |
| 131 | 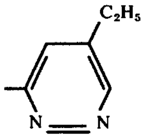 |
| 132 | 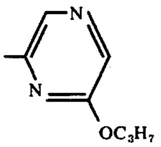 |
| 133 | 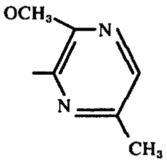 |
| 134 | 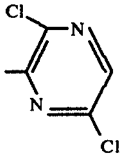 |
| 135 | 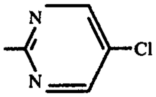 |
| 136 | 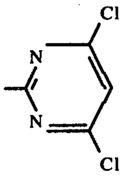 |
| 137 | 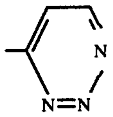 |
| 138 | 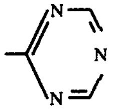 |
| 139 | 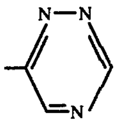 |
-continued
| Col. I | Col. II |
|---|---|
| 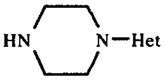 | 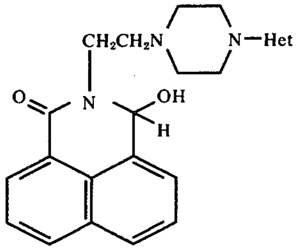 |
| Ex. | Het |
| 140 | 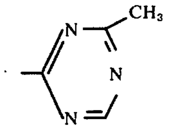 |
| 141 | 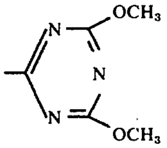 |
| 142 | 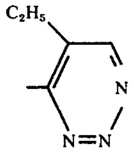 |
| 143 | 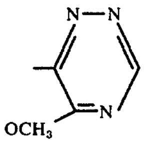 |
| 144 | 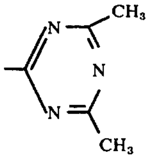 |
| 145 | 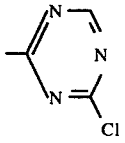 |
| 146 | 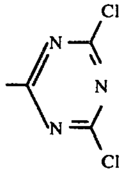 |
Similarly, by employing the substituted piperazines of examples 115 to 146 in the procedures of examples 113 and 114, other compounds within the scope of the invention are obtained.

EXAMPLE 147

5 (and/or 8)-Chloro-2-[2-(3,6-dihydro-4-phenyl-1(2H)-pyridinyl)-ethyl]-2,3-dihydro-3-hydroxy-1H-benz-[de]isoquinolin-1-one a. 5-Chloro-2-(2-hydroxyethyl)-1H-benz[de]isoquinoline-1,3(2H)-dione, 4-methylbenzenesulfonate ester Following the procedure of example 1(a) and (b) but substituting 3-chloronaphthalic anhydride for the naphthalic anhydride one obtains 5-chloro-2-(2-hydroxyethyl)-1H-benz[de]isoquinoline-1,3(2H)-dione, 4-methylbenzenesulfonate ester.

b. 5-Chloro-2-[2-(3,6-dihydro-4-phenyl-1(2H)-pyridinyl)ethyl]-1H-benz[de]isoquinoline-1,3(2H)-dione, hydrochloride (1:1)

10 g. (0.0234 mole) of the ester from part (a) and 7.5 g. (0.047 mole) of 4-phenyl-1,2,3,6-tetrahydropyridine (freed from the salt with aqueous NaOH, extracted into toluene and dried over 4A molecular sieves) are refluxed in 300 ml. of toluene for three hours. The mixture is then cooled to 25° for one hour and the resulting precipitate filtered off. The filrate is shaken with excess 10% HCl (aqueous) producing a gum that is insoluble in both layers. After several minutes the gum crystallizes and is filtered from the two liquid phases. Recrystallization of the filter cake is accomplished by dissolving the salt in 1000 ml. of hot chloroform, evaporating down to 300 ml., adding 300 ml. of hot abs. ethanol cooling and filtering off the resulting precipitate. Drying at 90° (0.1 mm.) for three hours yields 2.8 g. of 5-chloro-2-[2-(3,6-dihydro-4-phenyl-1(2H)-pyridinyl-)ethyl]-1H-benz[de]isoquinoline-1,3(2H)-dione, hydrochloride (1:1); m.p. 273°-275° (dec.).

c. 5 (and/or 8)-Chloro-2-[2-(3,6-dihydro-4-phenyl-1(2H)-pyridinyl)ethyl]-2,3-dihydro-3-hydroxy-1H-benz[de]isoquinolin-1-one Treating the hydrochloride salt product from part (b) according to the procedure set forth in example 1(d) yields the titled compound.

EXAMPLE 148

5 (and/or 8)-Chloro-2-[2-(4-phenyl-1-piperazinyl)ethyl]-2,3-dihydro-3-hydroxy-1H-benz[de]isoquinolin-1-one a. 5-Chloro-2-[2-(4-phenyl-1-piperazinyl)ethyl]-1H-benz[de]isoquinoline-1,3(2H)-dione, hydrochloride (1:1)

10 g. (0.023 mole) of the ester from example 147(a) and 7.6 g. (0.049 mole) of N-phenylpiperazine are refluxed in 300 ml. of toluene for one hour. The mixture is then cooled to 25° and after three hours the resulting precipitate is removed by filtration. The filtrate is shaken with excess 10% HCl (aqueous) producing a gum that is insoluble in both layers. After several minutes the gum crystallizes and is filtered from the two liquid phases. This crude material is digested for two hours at reflux temperature in 1000 ml. of 50% aqueous ethanol, cooled to 25°, filtered, and dried at 90° (0.1 mm.) for four hours to yield 5.2 g. of 5-chloro-2-[2-(4-phenyl-1-piperazinyl)ethyl]-1H-benz-[de]isoquinoline-1,3(2H)-dione, hydrochloride (1-1); preliminary darkening at 284° followed by melting with decomposition at 286°-290°.

b. 5 (and/or 8)-Chloro-2-[2-(4-phenyl-1-piperazinyl)ethyl]-2,3-dihydro-3-hydroxy-1H-benz[de]isoquinolin-1-one Treating the hydrochloride salt product from part (a) according to the procedure of example 88(b) yields the titled compound.

EXAMPLE 149

6 (and/or 7)-Chloro-2-[2-(4-phenyl-1-piperazinyl)ethyl]-2,3-dihydro-3-hydroxy-1H-benz[de]isoquinolin-1-one a. 6-Chloro-2-(2-chloroethyl)-1H-benz[de]isoquinoline-1,3(2H)-dione 25 g. (0.108 mole) of 4-chloronaphthalimide is dissolved in 300 ml. of warm dimethylformamide (ca. 80°). 7.1 g. (0.108 mole) of potassium hydroxide (85%) in 100 ml. of ethanol is added resulting in the formation of a precipitate. The resulting mixture is heated at about 90° for 30 minutes and 45 g. (0.32 mole) of 1-bromo-2-chloroethane in 100 ml. of dimethylformamide is added. After stirring for one hour, the mixture is cooled, poured into three liters of water and extracted with $CHCl_3$. The chloroform solution is evaporated to dryness and washed through a short (100 g.) column of alumina (Act. I) with $CHCl_3$. The solvent is removed under vacuum and the residue is digested for 30 minutes in boiling ethanol. The mixture is cooled to 25° and the precipitate is filtered off and dried to yield 13.6 g. of 6-chloro-2-(2-chloroethyl)-1H-benz-[de]isoquinoline-1,3(2H)-dione.

b. 6-Chloro-2-[2-(4-phenyl-1-piperazinyl)ethyl]-1H-benz[de]isoquinoline-1,3(2H)-dione, hydrochloride (1:1)

5 g. (0.017 mole) of 6-chloro-2-(2-chloroethyl)-1H-benz[de]isoquinoline-1,3(2H)-dione, from part (a), 6 g. (0.037 mole) of N-phenylpiperazine, and 2.2 g. (0.017 mole) of diisopropylethylamine are refluxed in 250 ml. of toluene for 48 hours. After cooling to 25°, the mixture is shaken with excess 10% HCl producing a precipitate that is insoluble in both liquid phases. The precipitated crude product is filtered off and purified by converting it back to the free base (partition between 10% KOH and $CHCl_3$ and evaporating off the $CHCl_3$) and then washing it through a short column of alumina (50 × 170 mm. Act. I) with $CHCl_3$. The solvent is removed to give 3 g. of free base. This is again taken up in toluene and converted to the salt by shaking with 10% HCl (aqueois). The resulting precipitate is filtered from the two liquid phases, recrystallized from 66% aqueous ethanol, and dried for 12 hours at 70° (0.1 mm.) to yield 2.0 g. of 6-chloro-2-[2-(4-phenyl-1-piperazinyl)ethyl]-1H-benz[de]isoquinoline-1,3(2H)-dione, hydrochloride (1:1).

The melting point of the salt is indistinct. On rapid heating (10°-20°/minute), from 200°-265° the material changes color from yellow to gray to black. On slower heating from 265°-272° the black material collapses and at 272°-274° becomes fluid.

c. 6 (and/or 7)-Chloro-2-[2-(4-phenyl-1-piperazinyl)ethyl]-2,3-dihydro-3-hydroxy-1H-benz[de]isoquinolin-1-one Treating the hydrochloride salt product from part (b) according to the procedure of example 88(b) yields the titled compound.

EXAMPLES 150-177

Following the procedures of examples 1, 38, 66, 88 or 112 but substituting for the 2-(2-hydroxyethyl)-1H-benz[de]-isoquinoline-1,3(2H)-dione, 4-methylbenzenesulfonate ester the ester shown below in Col. I one obtains the products shown in Col. II, III, IV, V, or VI, respectively. When the compound of Col. I is unsymmetric the product obtained is a mixture as in Examples 147 to 149 (separable by chromatographic means) since either keto group can be reduced.

Col. I

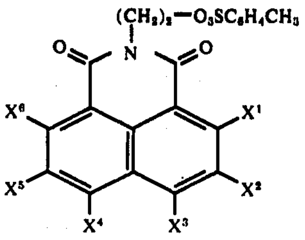

Col. II

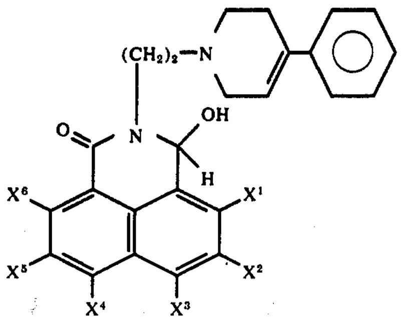

Col. III

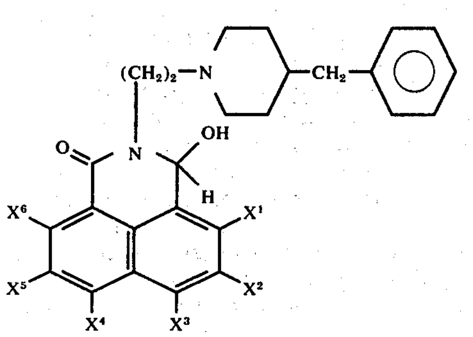

Col. IV

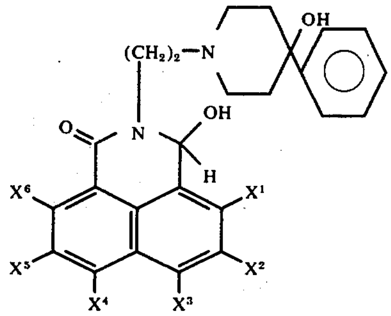

Col. V

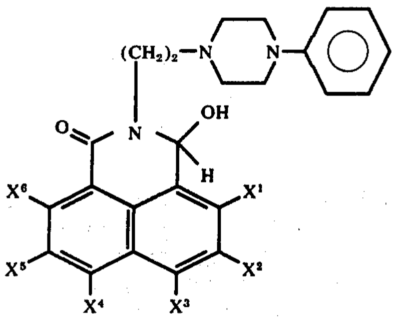

Col. VI

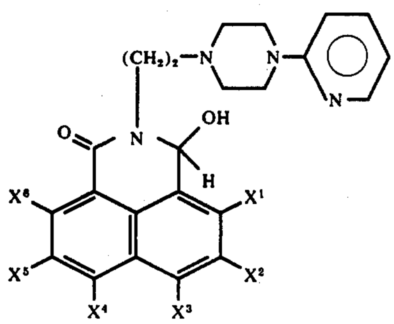

| Ex. | $X^1$ ($X^6$) | $X^2$ ($X^5$) | $X^3$ ($X^4$) | $X^4$ ($X^3$) | $X^5$ ($X^2$) | $X^6$ ($X^1$) |
|---|---|---|---|---|---|---|
| 150 | H | H | Cl | H | H | H |
| 151 | H | Cl | H | H | H | H |
| 152 | H | Br | H | H | H | H |
| 153 | H | F | H | H | H | H |
| 154 | H | I | H | H | H | H |
| 155 | H | Cl | H | H | Cl | H |
| 156 | Br | H | H | H | H | H |
| 157 | H | H | Cl | Cl | H | H |
| 158 | H | H | $CH_3$ | H | H | H |
| 159 | H | H | $C_2H_5$ | H | H | H |
| 160 | H | H | i-$C_3H_7$ | H | H | H |
| 161 | H | H | $CH_3$ | $CH_3$ | H | H |
| 162 | H | H | $OCH_3$ | H | H | H |
| 163 | H | H | $OC_2H_5$ | H | H | H |
| 164 | H | H | $OC_3H_7$ | H | H | H |
| 165 | H | H | $OCH_3$ | $OCH_3$ | H | H |
| 166 | H | $NO_2$ | H | H | H | H |
| 167 | H | H | $NO_2$ | H | H | H |
| 168 | H | $CF_3$ | H | H | H | H |
| 169 | H | H | $CF_3$ | H | H | H |
| 170 | H | CN | H | H | H | H |
| 171 | H | H | CN | H | H | H |
| 172 | H | H | $NH_2$ | H | H | H |
| 173 | H | $NH_2$ | H | H | H | H |
| 174 | H | $SC_2H_5$ | H | H | H | H |

-continued

| | | | | | | |
|---|---|---|---|---|---|---|
| 175 | H | H | $SCH_3$ | H | H | H |
| 176 | H | $CH_3$ | H | H | $CH_3$ | H |
| 177 | H | Br | H | H | Br | H |

Similarly, by employing the esters of Col. I of examples 150–177 in the procedures of examples 6 to 28, 39, 45 to 65, 71 to 87, 91 to 111, or 115 to 146, other compounds within the scope of this invention are obtained.

Also, by following the procedures of examples 4 to 5, 41 to 43, 68 to 70, 90, or 114, but employing a substituted 1,8-naphthalimide of formula VIII wherein the substituents are those listed under the headings $X^1$, $X^2$, $X^3$, $X^4$, $X^5$, and $X^6$ in examples 150 to 177, other compounds within the scope of this invention are obtained.

Also, by following the procedures of examples 2, 3, 29 to 37, 40, 67, 89, or 113, but employing a substituted 1,8-naphthalic anhydride of formula III wherein the substituents are those listed under the headings $X^1$, $X^2$, $X^3$, $X^4$, $X^5$ and $X^6$ in examples 150 to 177, other compounds within the scope of the invention are prepared.

What is claimed is:

1. A compound of the formula:

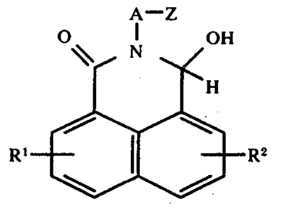

wherein $R^1$ and $R^2$ are independently selected from the group consisting of hydrogen, halogen, lower alkyl, lower alkoxy, lower alkylthio, trifluoromethyl, nitro, amino and cyano; Z is selected from the group consisting of

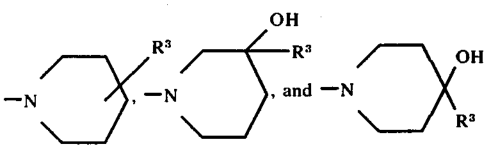

wherein the dashed line indicates the optional presence of a double bond; $R^3$ is selected from the group consisting of phenyl, phenyl-lower alkyl, substituted phenyl and substituted phenyl-lower alkyl wherein said substituent is one or two members selected from the group consisting of lower alkyl, lower alkoxy, lower alkylthio, halogen, amino, nitro, and trifluoromethyl provided that only one phenyl substituent is selected from amino, nitro, trifluoromethyl, and lower alkylthio; and A is straight or branched chain alkylene of 2 to 8 carbons.

2. The compound of claim 1 of the formula:

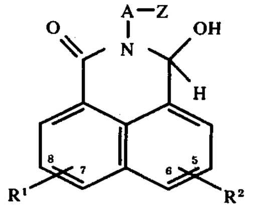

wherein $R^1$ and $R^2$ are the same and are located at the 7- and 6-positions or the 8- and 5-positions respectively and are selected from the group consisting of hydrogen, lower alkyl of 1 to 4 carbons, lower alkoxy of 1 to 4 carbons, lower alkylthio of 1 to 4 carbons, trifluoromethyl, halogen, amino, nitro and cyano; and $R^3$ is selected from the group consisting of phenyl, phenyl-lower alkyl, substituted phenyl, and substituted phenyl-lower alkyl wherein said lower alkyl is of 1 to 4 carbons and said phenyl substituent is one or two members selected from the group consisting of lower alkyl of 1 to 4 carbons, lower alkoxy of 1 to 4 carbons, lower alkylthio of 1 to 4 carbons, halogen, amino, nitro and trifluoromethyl provided that only one phenyl substituent is selected from amino, nitro, trifluoromethyl, and lower alkylthio.

3. The compound of claim 2 wherein $R^1$ and $R^2$ are selected from the group consisting of hydrogen, Cl, Br, F, methyl and methoxy; Z is

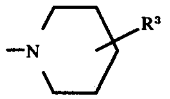

wherein the dashed line indicates the optional presence of a double bond; $R^3$ is selected from the group consisting of phenyl, benzyl, phenethyl, monosubstituted phenyl, monosubstituted benzyl, and monosubstituted phenethyl wherein said substituent is Cl, Br, F, methyl or methoxy; and A is straight or branched chain alkylene of 2 to 6 carbons.

4. The compound of claim 3 wherein $R^1$ and $R^2$ are both hydrogen; Z is

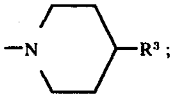

and A is straight chain alkylene of 2 to 6 carbons.

5. The compound of claim 4 wherein A is $-(CH_2)_2-$.

6. The compound of claim 4 wherein A is $-(CH_2)_3-$.

7. The compound of claim 4 wherein A is $-(CH_2)_4-$.

8. The compound of claim 4 wherein A is $-(CH_2)_5-$.

9. The compound of claim 4 wherein A is $-(CH_2)_6-$.
10. The compound of claim 3 wherein $R^1$ and $R^2$ are both hydrogen; Z is
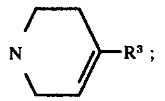
and A is straight chain alkylene of 2 to 6 carbons.
11. The compound of claim 10 wherein A is $-(CH_2)_2-$.
12. The compound of claim 10 wherein A is $-(CH_2)_3-$.
13. The compound of claim 10 wherein A is $-(CH_2)_4-$.
14. The compound of claim 10 wherein A is $-(CH_2)_5-$.
15. The compound of claim 10 wherein A is $-(CH_2)_6-$.
* * * * *

UNITED STATES PATENT AND TRADEMARK OFFICE

CERTIFICATE OF CORRECTION

PATENT NO. : 4,007,191

DATED : February 8, 1977

INVENTOR(S) : Wade et al.

It is certified that error appears in the above-identified patent and that said Letters Patent are hereby corrected as shown below:

The title should read -- 2-[(PIPERIDINYL OR TETRAHYDROPYRIDINYL)ALKYL]-2,3-DIHYDRO-3-HYDROXY-1H-BENZ[de]ISOQUINOLIN-1-ONES --.

In the abstract, "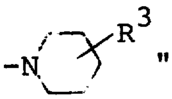" should read -- 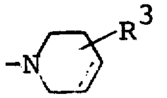 --.

In the abstract, second line from bottom, "chainalkylene" should read --chain alkylene--.

Col. 1, line 30, "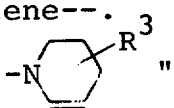" should read -- 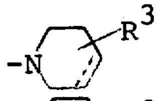 --.

Col. 2, line 50, "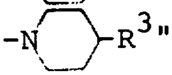" should read -- 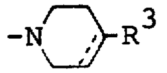 --.

Col. 5, line 20, "(66)." should read -- 66). --.

Col. 5, line 37, "ethyl[" should read --ethyl]--.

Col. 5, line 40, "2-[4-(3,6-Dihydro-4-phenyl)-1-(2H)-pyridinyl)-" should read --2-(2-Hydroxyethyl)-1H-benz[de]isoquinoline- --.

Col. 5, line 62, "1-(2H)" should read -- 1(2H) --.

Col. 6, line 37, "isoquinoline" should read --isoquinolin--.

Col. 7, line 35, "1-(2H)" should read -- 1(2H) --.

Col. 8, line 20, "2-[6 (3,6-" should read --2-[6-(3,6- --.

Col. 8, line 31, "1-(2H)" should read -- 1(2H) --.

UNITED STATES PATENT OFFICE

CERTIFICATE OF CORRECTION

Patent No. 4,007,191 Dated February 8, 1977

Inventor(s) Peter C. Wade et al.

It is certified that error appears in the above-identified patent and that said Letters Patent are hereby corrected as shown below:

Col. 9, line 11, "3,6dihydro" should read --3,6-dihydro--.

Col. 10, line 16, "lone" should read --1-one--.

Col. 10, line 30, "lone" should read --1-one--.

Col. 11, line 38, "piperidinyl]-2,3" should read --piperidinyl]-ethyl]-2,3--.

Col. 14, line 51, "2-[2-(2-phenylethyl)" should read --2-[2-[2-(2-phenylethyl)--.

Col. 14, line 60, "2-[2-[4-(4-nitrophenyl)" should be deleted, and --2-[2-[4-(3,4-dichlorophenyl)-- should be inserted in its place.

Col. 17, line 20, "ethhyl" should read --ethyl--.

Col. 18, line 1, "piperzinyl" should read --piperazinyl--.

Col. 18, line 2, "isoquinoline" should read --isoquinolin--.

UNITED STATES PATENT OFFICE
CERTIFICATE OF CORRECTION

Patent No. 4,007,191 Dated February 8, 1977

Inventor(s) Peter C. Wade et al

It is certified that error appears in the above-identified patent and that said Letters Patent are hereby corrected as shown below:

Col. 28, line 46, "aqueois" should read --aqueous--.

Col. 31, line 53, "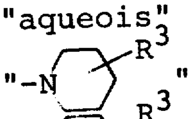" should read -- 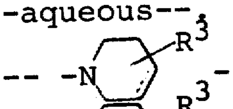 --.

Col. 32, line 40, "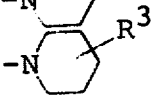" should read -- 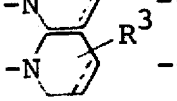 --.

Signed and Sealed this

Twenty-eighth Day of June 1977

[SEAL]

*Attest:*

RUTH C. MASON
*Attesting Officer*

C. MARSHALL DANN
*Commissioner of Patents and Trademarks*